United States Patent
Wagner

(10) Patent No.: US 9,130,239 B2
(45) Date of Patent: Sep. 8, 2015

(54) PROCESS FOR MANUFACTURING PHOSPHATE ESTERS FROM PHOSPHORYL CHLORIDE AND MONOALKYL ETHERS OF GLYCOLS OR POLYGLYCOLS

(75) Inventor: Nicole L. Wagner, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 30 days.

(21) Appl. No.: 13/395,913

(22) PCT Filed: Sep. 24, 2010

(86) PCT No.: PCT/US2010/050100
§ 371 (c)(1),
(2), (4) Date: Mar. 14, 2012

(87) PCT Pub. No.: WO2011/043934
PCT Pub. Date: Apr. 14, 2011

(65) Prior Publication Data
US 2012/0172613 A1    Jul. 5, 2012

Related U.S. Application Data

(60) Provisional application No. 61/248,831, filed on Oct. 5, 2009.

(51) Int. Cl.
| | |
|---|---|
| *H01M 10/052* | (2010.01) |
| *C07F 9/09* | (2006.01) |
| *C07F 9/24* | (2006.01) |
| *C07F 9/40* | (2006.01) |
| *H01M 10/0567* | (2010.01) |
| *H01M 10/0569* | (2010.01) |

(52) U.S. Cl.
CPC ............ *H01M 10/052* (2013.01); *C07F 9/091* (2013.01); *C07F 9/2408* (2013.01); *C07F 9/4006* (2013.01); *H01M 10/0567* (2013.01); *H01M 10/0569* (2013.01); *Y02E 60/122* (2013.01)

(58) Field of Classification Search
CPC .......... C07F 9/09; C07F 9/091; C07F 9/2408; C07F 9/4006; H01M 10/052; H01M 10/0567; H01M 10/0569
USPC .................................. 558/101, 186
See application file for complete search history.

(56) References Cited

U.S. PATENT DOCUMENTS

| | | | | |
|---|---|---|---|---|
| 3,005,007 | A | * | 10/1961 | Fierce et al. .................. 558/100 |
| 3,769,221 | A | * | 10/1973 | Burrous ....................... 252/78.5 |
| 5,393,621 | A | | 2/1995 | Chaloner-Gill |
| 5,830,600 | A | | 11/1998 | Narang |
| 6,642,294 | B1 | | 11/2003 | Bauer |
| 6,727,343 | B2 | | 4/2004 | Morris |
| 2009/0163446 | A1 | * | 6/2009 | Hanson et al. .................. 514/92 |

FOREIGN PATENT DOCUMENTS

| | | | |
|---|---|---|---|
| CN | 101148457 | * | 3/2008 |
| EP | 906641 | B | 4/1999 |
| EP | 1357628 | A | 10/2003 |
| WO | 97/44842 | A | 11/1997 |

OTHER PUBLICATIONS

Translation of CN101148457, pp. 1-6.*
Morford et al., "A fire-resistant organophosphorous gel polymer . . . " Solid State Ionics 133 (2000) 171-177.

* cited by examiner

*Primary Examiner* — Paul A Zucker
*Assistant Examiner* — Mark Luderer
(74) *Attorney, Agent, or Firm* — Gary C Cohn PLLC

(57) ABSTRACT

Phosphate ester compounds are prepared by reacting phosphoryl chloride with at least one mono(alkylene glycol) monoether or poly(alkylene glycol) monoether, or a mixture at least one mono(alkylene glycol) monoether or poly(alkylene glycol) monoether and at least one alkylene glycol or polyalkylene glycol, in the presence of at least three moles per mole of phosphoryl chloride of a pyridinyl compound that is devoid of aliphatic nitrogen atoms.

2 Claims, 1 Drawing Sheet

PROCESS FOR MANUFACTURING PHOSPHATE ESTERS FROM PHOSPHORYL CHLORIDE AND MONOALKYL ETHERS OF GLYCOLS OR POLYGLYCOLS

This application claims priority from U.S. Provisional Application No. 61/248,831, filed 5 Oct. 2009.

The present invention relates to a method for producing phosphate esters from phosphoryl chloride (POCl$_3$, phosphorus chloride oxide) and monoalkyl ethers of glycols or polyglycols.

Phosphate compounds having the general structure

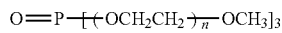

with n being 1 or 2 have been suggested for use as additives in battery electrolyte solutions. See, for example, U.S. Pat. No. 6,642,294, EP 906 641 and *Solid State Ionics* 133, 2000, 171-177. These phosphate compounds may impart some desirable mechanical, thermal and electrical properties to the electrolyte solution and to a battery containing the electrolyte solution. They may provide flame retardance, which is of great significance, especially with respect to lithium batteries, because these batteries contain non-aqueous electrolytes and also because they have high energy and power densities. The organic nature of the electrolyte, coupled with the high energy and power densities, makes lithium batteries very susceptible to thermal runaway events, such as runaway exothermic reactions and even fires. Flame retardants are routinely incorporated into lithium battery electrolytes for this reason.

Phosphate compounds having the foregoing structure have been prepared in a reaction between phosphoryl chloride and ethylene glycol monomethyl ether, (i.e., HOCH$_2$CH$_2$OCH$_3$) or diethylene glycol monomethyl ether (i.e., HO(CH$_2$CH$_2$O)$_2$CH$_3$). U.S. Pat. No. 6,642,294 describes conducting this reaction neat (i.e., without solvent) in the presence of a zinc chloride catalyst. A product mixture is obtained, which then undergoes multiple distillation steps in order to isolate the desired phosphate product. In EP 906641, the reaction is conducted in the presence of 4-dimethylamino pyridine. Yields are poor (56%) and the product is a mixture of materials from which the desired product is recovered chromatographically.

*Solid State Ionics*, 133, 2000, 171-177, describes conducting the reaction in the presence of triethylamine. Triethylamine scavenges the HCl by-product that is formed in the reaction. This approach is not very selective, as a variety of phosphorus-containing reaction products, including some phosphorus-nitrogen compounds, are produced. This leads to a significant waste of raw materials, and in addition considerable efforts are needed to isolate the desired product from the other components of reaction mixture.

For these reasons, these synthetic processes are not well-suited for implementation at large scale. Therefore, a method by which these phosphate compounds can be prepared with low levels of impurities is desired.

This invention is such a process. This invention is a process for forming phosphate ester compounds, comprising reacting phosphoryl chloride with at least one mono(alkylene glycol) monoether or poly(alkylene glycol) monoether, or a mixture at least one mono(alkylene glycol) monoether or poly(alkylene glycol) monoether with at least one alkylene glycol or polyalkylene glycol, in the presence of at least three moles, per mole of phosphoryl chloride, of a pyridinyl compound that is devoid of aliphatic nitrogen atoms. This process forms the corresponding triphosphate compounds in good yields. The process is very selective to the desired triphosphate compounds. Undesired side reactions that consume phosphorus tend to be minimized with this process. This reduces the loss of starting materials to unwanted by-products and also simplifies recovery of the product from the reaction mixture.

Figure 1:
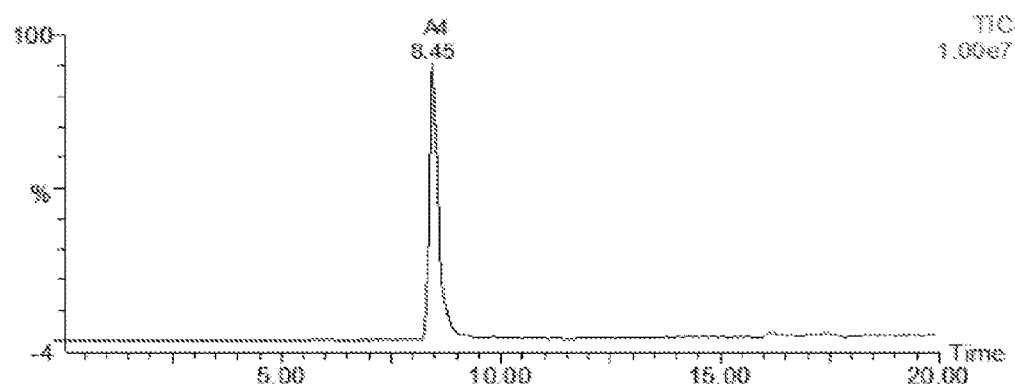
FIG. 1. The liquid chromatography/mass spectroscopy of the phosphorylation in THF and pyridine.

Suitable mono(alkylene glycol) monoethers include monoalkyl ethers of 1,2-ethylene glycol, 1,2-propylene glycol, 1,3-propylene glycol, 1,2-butylene glycol, 1,4-butylene glycol (tetramethylene glycol), hexamethylene glycol, and the like. The alkyl group preferably contains from 1 to 4 carbon atoms and is most preferably methyl. The monoalkyl ether will contain one hydroxyl group which can react with phosphoryl chloride to form an ester. Ethylene glycol monomethyl ether is especially preferred among the mono (alkylene glycol) monoethers.

Suitable poly(alkylene glycol) monoethers include monoalkyl ethers of polyethylene glycol, poly-1,2-propylene glycol, poly-1,3-propylene glycol, poly-1,2-butylene glycol, poly-1,4-butylene glycol (polytetramethylene glycol), or poly(hexamethylene glycol), or a copolymer of any two or more of 1,2-ethylene glycol, 1,2-propylene glycol, 1,3-propylene glycol, 1,2-butylene glycol, 1,4-butylene glycol (tetramethylene glycol) and hexamethylene glycol. The degree of polymerization is two or more, but preferably not greater than five. The alkyl group preferably contains from 1 to 4 carbon atoms and is most preferably methyl. These monoethers contain one hydroxyl group which can react with phosphoryl chloride to form an ester. Monoalkyl ethers of polymers and copolymers of 1,2-ethylene oxide are preferred. Monoalkyl ethers of diethylene glycol and/or triethylene glycol are especially preferred.

Mixtures of two or more mono(alkylene glycol) monoethers can be used, as can mixtures of two or more poly(alkylene glycol) monoethers. A mixture of one or more mono (alkylene glycol) monoethers with one or more poly(alkylene glycol) monoethers can be used.

The monoethers described before can be used in an admixture with at least one alkylene glycol or polyalkylene glycol. The alkylene glycols and polyalkylene glycols are as described before with respect to the monoethers, except of course that neither of the terminal hydroxyl groups are capped with a methyl group. The alkylene glycols and polyalkylene glycols therefore contain two hydroxyl groups per molecule, and can react difunctionally to form ester linkages with two phosphoryl chloride molecules. Thus, the alkylene glycol or polyalkylene glycol, when present, functions as a coupling agent, which can, if used in large proportions, lead to the formation of high molecular weight esters. Because of this, the alkylene glycols and polyalkylene glycols, if present at all, are present in relatively small proportions. It is preferred that no more than 1 mole of alkylene glycols and/or polyalkylene glycols be used per 4 moles of monoethers. Alkylene glycols and polyalkylene glycols can be omitted altogether.

Each mole of phosphoryl chloride will react with three equivalents of hydroxyl groups. Therefore, at least three equivalents of the monoether, or monoether/glycol mixture, are present in the reaction mixture for each mole of phosphoryl chloride. It is generally preferred to provide an excess of the monoether or monoether/glycol mixture. Thus for example, from 3 to 10, preferably from 4 to 6 equivalents of the monoether or monoether/glycol mixture can be provided per mole of phosphoryl chloride.

The reaction of the monoether or monoether/glycol mixture with phosphoryl chloride is conducted in the presence of a pyridinyl compound which does not contain aliphatic nitrogen atoms. The pyridinyl compound is believed to function as a scavenger for HCl, which is produced in the esterification reaction. Enough of the pyridinyl compound should be present to consume all of the HCl which is produced. Therefore, it is preferred to provide at least three moles of the pyridinyl compound per mole of phosphoryl chloride. An excess of the pyridinyl compound is preferred. Therefore, from 3 to 10, preferably 3.1 to 6 moles of the pyridinyl compound can be provided per mole of phosphoryl chloride.

The pyridinyl compound contains at least one moiety having the structure:

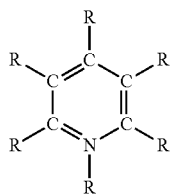

wherein the R groups are independently hydrogen, alkyl, aryl, aryl-substituted alkyl, and the like. Two or more of the R groups may form, together with the carbon atoms to which they are attached (and any intervening carbon atoms in the aromatic ring, if any), a fused ring structure. The fused rings may be aromatic or aliphatic. Any substituents should be devoid of aliphatic nitrogen atoms, although additional nitrogen atom(s) that form part of an aromatic ring structure may be present. It is preferred that all R groups are hydrogen, in which case the pyridinyl compound is pyridine.

The reaction may be conducted neat (i.e., solventless) or in the presence of a solvent. It is generally preferred to use a solvent, as the HCl salt of the pyridinyl compound that forms as the reaction proceeds will in most cases precipitate from the reaction; without a solvent, the presence of this solid phase may cause the reaction mixture to be too viscous to handle easily. A suitable solvent is a solvent for the monoether or monoether/glycol mixture, as the case may be, and for the product phosphate ester and the pyridinyl compound, but should be a material in which the HCl salt of the pyridinyl compound is essentially insoluble. The solvent should of course not react with any of the starting materials, the product or reaction by-products under the conditions of the reaction. A variety of organic solvents are useful, including non-polar types such as aliphatic or aromatic hydrocarbons and polar types such as tetrahydrofuran and 1,2-dichloroethane. Polar types are generally preferred, as the reaction tends to proceed more rapidly and under milder conditions in polar solvents. The amount of solvent that is used is not considered to be critical.

The reaction can be conducted under mild conditions. It is often beneficial to add the phosphoryl chloride to the monoether or monoether/glycol mixture. The pyridinyl compound is preferably present at the time that the phosphoryl chloride is first mixed with the monoether or monoether/glycol mixture, but it can be added afterwards, but before the reaction has completed. If a solvent is used, the monoether or monoether/glycol mixture is preferably dissolved into the solvent prior to commencing the reaction. The phosphoryl chloride may be added gradually to the monoether or monoether/glycol mixture in order to prevent a rapid temperature increase due to the exothermic reaction. The temperature at the time of mixing the phosphoryl chloride and monoether or monoether/glycol mixture may be below, at, or above room temperature. For example, the reactants may be brought to a temperature of from −20° to 24° C. or from −10° C. to +10° C. prior to contacting them with each other. In other embodiments, the reactants can be brought into contact while at a temperature of from 20 to 40° C., or at a higher temperature of from 40 to 120° C. Cooler temperatures are preferred.

After the phosphoryl chloride/monoether or monoether/glycol mixture/pyridinyl compound mixture has been formed, the mixture may be brought to a temperature of from, for example, 0 to 120° C. to permit the reaction to continue. A temperature of from 20 to 50° C. often is suitable. Some reaction typically occurs immediately after the reaction mixture is formed, as indicated by the formation of precipitated HCl salt of the pyridinyl compound. The reaction may take several hours to complete, with the amount of time being dependent on reaction temperature and to some extent the choice of solvent. Reaction rates tend to be higher in a polar solvent such as tetrahydrofuran or 1,2-diethylene chloride, than in a non-polar solvent such as toluene.

The phosphoryl chloride and monoether or monoether/glycol mixture react to form a phosphate ester compound. This phosphate ester compound is suitably a triester corresponding to the reaction of phosphoryl chloride with three moles of the alcohols. Such a product can be represented by the structure

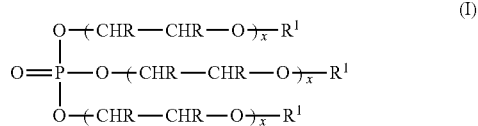
(I)

wherein each x is independently 1 or more, each R is hydrogen or alkyl, and each $R^1$ is alkyl or

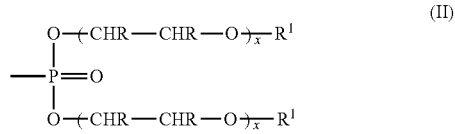
(II)

When an alkylene glycol or polyalkylene glycol is present in the reaction mixture, some of the $R^1$ groups will have the structure II. Otherwise, the $R^1$ groups will be alkyl, and will correspond to the terminal alkyl groups on the monoether compound. At least some of the $R^1$ groups are alkyl groups.

It is preferred that each x is from 1 to 5 and more preferred that each x is from 1 to 3. Each R is preferably hydrogen or $C_{1-2}$ alkyl. R is more preferably hydrogen in each case. It is preferred that no more than one $R^1$ group has structure II, and the remainder are $C_{1-4}$ alkyl, especially methyl. It is more preferred that each $R^1$ group is $C_{1-4}$ alkyl, and still more preferred that each $R^1$ group is methyl.

The crude reaction mixture will contain, in addition to the phosphate ester product described above: the HCl salt of the pyridinyl compound, which in most cases will precipitate from the reaction mixture as it forms; solvent, if any is used; and unreacted starting materials, particularly if the monoether, monoether/glycol mixture and/or the pyridinyl compound are used in excess. Some other phosphate ester compounds, including phosphorus-nitrogen compounds of the type described in Example 1 below, may form in the reaction. These compounds, which are formed in significant quantities when amines such as triethylamine are used as HCl scavengers, tend to form in very small quantities if at all in the process of this invention. The liquid phase of the crude reaction mixture tends to be colorless or nearly colorless, due to the absence or near-absence of these phosphorus-containing impurities.

Product recovery is simplified because the unwanted phosphate ester products are not produced in significant amounts. The HCl salt of the pyridinyl compound is easily separated out using any convenient solid-liquid separation technique such as filtration or centrifugation. Solvent, excess amounts of the pyridinyl compound and unreacted monoethers and glycols can be distilled from the product, under atmospheric or subatmospheric pressures. Further purification can be performed chromatographically by passing a solution of the phosphate ester product through a chromatography column in which a material such as alumina serves as the stationary phase. In such a case, the phosphate ester product that is recovered after removal of solvent and unreacted starting materials can be re-dissolved in a suitable solvent, such as acetonitrile or any of those mentioned before, to form a solution for chromatographic separation.

The phosphate ester product is useful as a component of a battery electrolyte solution, especially for a lithium battery. The phosphate ester may impart thermal stability and/or flame retardance to the electrolyte solution; it may also participate in SEI (solid electrolyte interface) formation at a carbon electrode. The alkylene glycol units in the phosphate ester compound are also believed to promote lithium ion conduction through the electrolyte during charge and discharge cycles. Battery electrolyte solutions that contain phosphate esters such as those produced with this invention are described in EP 906 641 and U.S. Pat. No. 6,642,294.

The battery electrolyte solution will contain, in addition to the phosphate ester, at least one lithium salt. The lithium salt may be any that is suitable for battery use, including inorganic lithium salts such as $LiAsF_6$, $LiPF_6$, $LiBF_4$, $LiB(C_2O_4)_2$, $LiBF_2C_2O_4$, $LiClO_4$, $LiBrO_4$ and $LiIO_4$ and organic lithium salts such as $LiB(C_6H_5)_4$, $LiCH_3SO_3$, $LiN(SO_2C_2F_5)_2$ and $LiCF_3SO_3$. $LiPF_6$, $LiClO_4$, $LiBF_4$, $LiAsF_6$, $LiCF_3SO_3$ and $LiN(SO_2CF_3)_2$ are preferred types, and $LiPF_6$ is an especially preferred lithium salt. The lithium salt is suitably present in a concentration of at least 0.5 moles/liter of electrolyte solution, preferably at least 0.75 moles/liter, up to 3 moles/liter and more preferably up to 1.5 moles/liter.

The battery electrolyte solution will in most cases also include at least one nonaqueous solvent for the lithium salt. The nonaqueous solvent may include, for example, one or more linear alkyl carbonates, cyclic carbonates, cyclic esters, linear esters, cyclic ethers, alkyl ethers, nitriles, sulfones, sulfolanes, siloxanes and sultones. Mixtures of any two or more of the foregoing types can be used. Cyclic esters, linear alkyl carbonates, and cyclic carbonates are preferred types of nonaqueous solvents.

Suitable linear alkyl carbonates include dimethyl carbonate, diethyl carbonate, methyl ethyl carbonate and the like. Cyclic carbonates that are suitable include ethylene carbonate, propylene carbonate, butylene carbonate and the like. Suitable cyclic esters include, for example, γ-butyrolactone and γ-valerolactone. Cyclic ethers include tetrahydrofuran, 2-methyltetrahydrofuran, tetrahydropyran and the like. Alkyl ethers include dimethoxyethane, diethoxyethane and the like. Nitriles include mononitriles, such as acetonitrile and propionitrile, dinitriles such as glutaronitrile, and their derivatives. Sulfones include symmetric sulfones such as dimethyl sulfone, diethyl sulfone and the like, asymmetric sulfones such as ethyl methyl sulfone, propyl methyl sulfone and the like, and their derivatives. Sulfolanes include tetramethylene sulfolane and the like.

Some preferred solvent mixtures include mixtures of a cyclic carbonate with a linear alkyl carbonate at a weight ratio of from 15:85 to 40:60; a cyclic carbonate/cyclic ester mixture at a weight ratio of from 20:80 to 50:50: a cyclic carbonate/cyclic ester/linear alkyl carbonate mixture at weight ratios of 20-48:50-78:2-20; cyclic ester/linear alkyl carbonate mixtures at a weight ratio of from 70:30 to 98:2.

Solvent mixtures of particular interest are mixtures of ethylene carbonate and propylene carbonate at a weight ratio of from 15:85 to 40:60; mixtures of ethylene carbonate and dimethyl carbonate at a weight ratio of from 15:85 to 40:60; mixtures of ethylene carbonate, propylene carbonate and dimethyl carbonate at a weight ratio of 20-48:50-78:2-20, and mixtures of propylene carbonate and dimethyl carbonate at a weight ratio of from 15:85 to 40:60.

Various other additives may be present in the battery electrolyte solution, in addition to the components already mentioned. These may include, for example, additives which promote the formation of a solid electrolyte interface at the surface of a graphite electrode; various cathode protection agents, lithium salt stabilizers, lithium deposition improving agents, ionic solvation enhancers, corrosion inhibitors, wetting agents and viscosity reducing agents. Many additives of these types are described by Zhang in "A review on electrolyte additives for lithium-ion batteries", *J. Power Sources* 162 (2006) 1379-1394.

Agents which promote solid electrolyte interface (SEI) formation include various polymerizable ethylenically unsaturated compounds, various sulfur compounds, as well as other materials. Suitable cathode protection agents include materials such as N,N-diethylamino trimethylsilane and $LiB(C_2O_4)_2$. Lithium salt stabilizers include LiF, tris(2,2,2-trifluoroethyl)phosphite, 1-methyl-2-pyrrolidinone, fluorinated carbamate and hexamethyl-phosphoramide. Examples of lithium deposition improving agents include sulfur dioxide, polysulfides, carbon dioxide, surfactants such as tetraalkylammonium chlorides, lithium and tetraethylammonium salts of perfluorooctanesulfonate, various perfluoropolyethers and the like. Crown ethers can be suitable ionic solvation enhancers, as are various borate, boron and borole compounds. $LiB(C_2O_4)_2$ and $LiF_2C_2O_4$ are examples of aluminum corrosion inhibitors. Cyclohexane, trialkyl phosphates and certain carboxylic acid esters are useful as wetting agents and viscosity reducers.

The various other additives may together constitute up to 20%, preferably up to 10%, of the total weight of the battery electrolyte solution.

The water content of the battery electrolyte solution should be as low as possible. A water content of 50 parts by million by weight (ppm) or less is desired and a more preferred water content is 30 ppm or less.

A battery containing the battery electrolyte solution can be of any useful construction. A typical battery construction includes an anode and cathode, with a separator and the electrolyte solution interposed between the anode and cathode so that ions can migrate through the electrolyte solution between the anode and the cathode. The assembly is generally packaged into a case. The shape of the battery is not limited. The battery may be a cylindrical type containing spirally-wound sheet electrodes and separators. The battery may be a cylindrical type having an inside-out structure that includes a combination of pellet electrodes and a separator. The battery may be a plate type containing electrodes and a separator that have been superimposed.

Suitable anode materials include, for example, carbonaceous materials such as natural or artificial graphite, carbonized pitch, carbon fibers, graphitized mesophase microspheres, furnace black, acetylene black and various other graphitized materials. The carbonaceous materials may be bound together using a binder such as a poly(vinylidene fluoride, polytetrafluoroethylene, a styrene-butadiene copolymer, an isoprene rubber, a poly(vinyl acetate), a poly(ethyl methacrylate), polyethylene or nitrocellulose. Suitable carbonaceous anodes and methods for constructing same are described, for example, in U.S. Pat. No. 7,169,511.

Other suitable anode materials include lithium metal, lithium alloys and other lithium compounds such as a lithium titanate anode.

Suitable cathode materials include inorganic compounds such as transition metal oxides, transition metal/lithium composite oxides, lithium/transition metal composite phosphates, transition metal sulfides, metal oxides, and transition metal silicates. Examples of transition metal oxides include MnO, $V_2O_5$, $V_6O_{13}$ and $TiO_2$. Transition metal/lithium composite oxides include lithium/cobalt composite oxides whose basic composition is approximately $LiCoO_2$, lithium/nickel composite oxides whose basic composition is approximately $LiNiO_2$, and lithium/manganese composite oxides whose basic composition is approximately $LiMn_2O_4$ or $LiMnO_2$. In each of these cases, part of the cobalt, nickel or manganese can be replaced with one or two metals such as Al, Ti, V, Cr, Fe, Co, Ni, Cu, Zn, Mg, Ga or Zr. Lithium/transition metal composite phosphates include lithium iron phosphate, lithium manganese phosphate, lithium cobalt phosphate, lithium iron manganese phosphate and the like. Examples of useful metal oxides include $SnO_2$ and $SiO_2$. Examples of useful metal silicates include lithium iron orthosilicate.

The electrodes are each generally in electrical contact with or formed onto a current collector. A suitable current collector for the anode is a metal or metal alloy such as copper, a copper alloy, nickel, a nickel alloy, stainless steel and the like. Suitable current collectors for the cathode include aluminum, titanium, tantalum, alloys of two or more of these and the like.

The separator is interposed between the anode and cathode to prevent the anode and cathode from coming into contact with each other and short-circuiting. The separator is conveniently a non-conductive material. It should not be reactive with or soluble in the electrolyte solution or any of the components of the electrolyte solution under operating conditions. Polymeric separators are generally suitable. Examples of suitable polymers for forming the separator include polyethylene, polypropylene, polybutene-1, poly-3-methylpentene, ethylene-propylene copolymers, polytetrafluoroethylene, polystyrene, polymethylmethacrylate, polydimethylsiloxane, polyethersulfones and the like.

The electrolyte solution must be able to permeate through the separator. For this reason, the separator is generally porous, being in the form of a porous sheet, nonwoven or woven fabric or the like. The porosity of the separator is generally 20% or higher, up to as high as 90%. A preferred porosity is from 30 to 75%. The pores are generally no larger than 0.5 microns, and are preferably up to 0.05 microns in their longest cross-sectional dimension. The separator is typically at least one micron thick, and may be up to 50 microns thick. A preferred thickness is from 5 to 30 microns.

The battery is preferably a secondary (rechargeable) lithium battery. In such a battery, the discharge reaction includes a dissolution or delithiation of lithium ions from the anode into the electrolyte solution and concurrent incorporation of lithium ions into the cathode. The charging reaction, conversely, includes an incorporation of lithium ions into the anode from the electrolyte solution. Upon charging, lithium ions are reduced on the anode side, at the same time, lithium ions in the cathode material dissolve into the electrolyte solution.

The battery can be used in industrial applications such as electric vehicles, hybrid electric vehicles, plug-in hybrid electric vehicles, aerospace, e-bikes, etc. The battery is also useful for operating a large number of electrical and electronic devices, such as computers, cameras, video cameras, cell phones, PDAs, MP3 and other music players, televisions, toys, video game players, household appliances, medical devices such as pacemakers and defibrillators, among many others.

The following examples are provided to illustrate the invention, but are not intended to limit the scope thereof. All parts and percentages are by weight unless otherwise indicated.

Example 1

Tetrahydrofuran is added to an argon-flushed round bottomed flask equipped with a stir bar and an addition funnel. Diethylene glycol monomethyl ether and pyridine are added to the flask and cooled to 0° C. in an ice bath. Phosphoryl chloride is then added dropwise with stirring. Proportions of ingredients are such that the resulting phosphoryl chloride starting concentration (i.e., after addition of phosphoryl chloride is completed) is about 0.5M, 6 equivalents of the monoether are provided per mole of phosphoryl chloride, and 5 moles of pyridine are provided per mole of phosphoryl chloride. Pyridine:HCl begins to precipitate as soon as the phosphoryl chloride addition begins. After the phosphoryl chloride addition is complete, the reaction mixture is allowed to warm to room temperature (25° C.) and stirred for about 24 hours.

The pyridine:HCl is filtered from the mixture, leaving a clear, colorless liquid phase behind. The solvent is removed in a rotary evaporator and the excess monoether and pyridine are distilled off under vacuum. The isolated product is dissolved in acetonitrile, passed through an alumina column, desolvated and dried under vacuum at 65° C.

The product is analyzed by liquid chromatography/mass spectroscopy. The results of this analysis are shown in FIG. 1. Only a single peak appears, at an elution time of about 8.45 minutes, of a material having a molecular weight of 404. This peak corresponds to a compound having the structure:

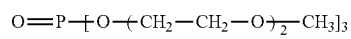

which is the desired tris(diethylene glycol monomethyl ether) ester of phosphoryl chloride.

Similar results are obtained when Example 1 is repeated neat or in 1,2-dichloroethane. When the reaction is performed in toluene, the mixture needs to be heated to reflux for several days in order to complete the reaction; the liquid chromatography/mass spectroscopy shows that the product in this case contains somewhat more impurities than in the other cases. This demonstrates the additional benefit of conducting the reaction in a polar solvent.

Comparative Run A

Example 1 is repeated, this time replacing pyridine with triethylamine. The reaction proceeds more slowly than in Example 1, requiring about 48 hours at room temperature to come to completion. A triethylamine:HCl salt that forms in the reaction is separated from the crude reaction mixture by filtration; the remaining liquid phase is highly colored. After removal of solvent, excess monoether and amine as described in Example 1, the product is re-dissolved in acetonitrile and passed through an alumina column, again as in Example 1. The product is then de-solvated and dried as in Example 1.

Figure 2:
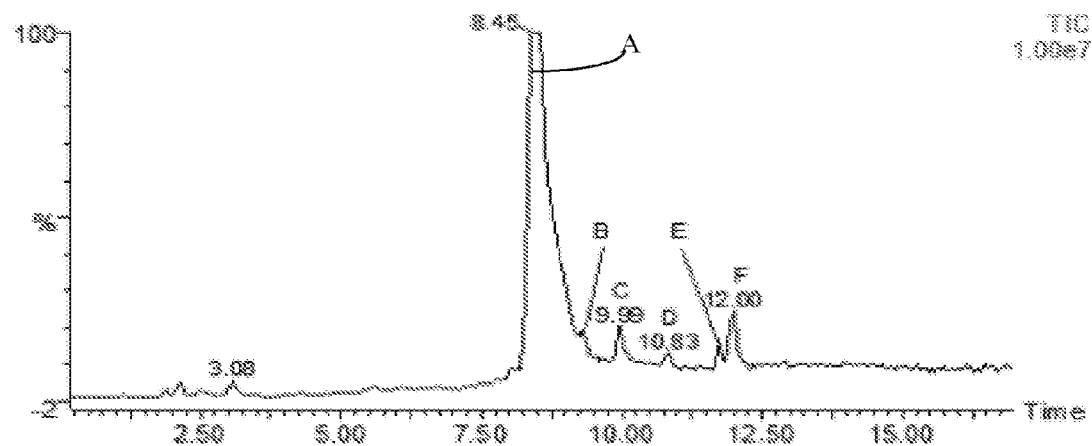
FIG. 2. The liquid chromatography/mass spectroscopy of the phosphorylation in THF and triethylamine.

Liquid chromatography/mass spectroscopy is performed, with the results being shown graphically in FIG. 2. As can be seen in FIG. 2, the obtained product is a mixture of compounds. The predominant peak is the 404 molecular weight material which represents the desired product. In addition, at least five other compounds are present in significant amounts. These include a 630 molecular weight compound identified as point B in FIG. 2; and compounds having molecular weights of 414, 357, 385 and 385, which are identified as points C through F in FIG. 2. The compounds represented by points D, E and F are phosphorus-nitrogen compounds; the point D and E compounds are believed to have the structures:

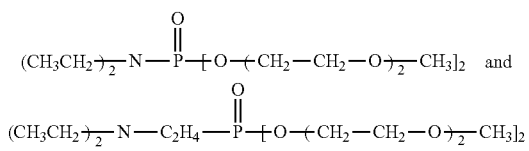

The compound identified by point F is believed to be an isomer of the compound of point E.

Example 2

Example 1 is repeated, this time substituting monoethylene glycol monomethyl ether for the diethylene glycol monomethyl ether used in Example 1. Liquid chromatography/mass spectroscopy is consistent with the product being the tris(monoethylene glycol monomethyl ether) ester of phosphoryl chloride. Essentially no other phosphorus compounds are detected. Similar results are also obtained when this experiment is repeated neat and in 1,2-dichloroethane.

Example 3

Example 1 is again repeated, this time substituting triethylene glycol monomethyl ether for the diethylene glycol monomethyl ether used in Example 1. Liquid chromatography/mass spectroscopy is consistent with the product being the tris(triethylene glycol monomethyl ether) ester of phosphoryl chloride. Essentially no other phosphorus compounds are detected. The product has a viscosity of 25 cPs at 25° C. Similar results are also obtained when this experiment is repeated neat and in 1,2-dichloroethane.

Thermal stability of the phosphate ester compounds obtained in Examples 1-3 is evaluated by thermogravimetric analysis (TGA). The sample is heated at the rate of 5° C./minute from 75° C., and weight loss is evaluated as a function of temperature. The temperature at which the sample has lost 50% of its initial (at 75° C.) weight is determined. The 50% weight loss temperature of the product of Example 2 is about 190° C. That of the Example 1 and 3 products are about 265° C. and 288° C., respectively.

What is claimed is:

1. A process for forming phosphate ester compounds, comprising reacting phosphoryl chloride with diethylene glycol monomethyl ether or triethylene glycol monomethyl ether in the presence of at least three moles per mole of phosphoryl chloride of a pyridinyl compound that is devoid of aliphatic nitrogen atoms, which reaction is performed in 1,2-dichloroethane as a solvent.

2. The process of claim 1 wherein the pyridinyl compound is pyridine.

* * * * *